(12) United States Patent
Oh et al.

(10) Patent No.: US 8,383,582 B2
(45) Date of Patent: Feb. 26, 2013

(54) INHIBITOR AGAINST FORMING BIOFILM COMPRISING κ-CASEIN MACROPEPTIDE

(75) Inventors: Sejong Oh, Gwangju (KR); Hyunsun Yun, Seoul (KR); Seahun Kim, Seoul (KR)

(73) Assignee: Industry Foundation of Chonnam National University, Gwangju (KR)

( * ) Notice: Subject to any disclaimer, the term of this patent is extended or adjusted under 35 U.S.C. 154(b) by 303 days.

(21) Appl. No.: 12/889,402

(22) Filed: Sep. 23, 2010

(65) Prior Publication Data
US 2012/0077736 A1 Mar. 29, 2012

(51) Int. Cl.
*A01N 37/18* (2006.01)
*A61K 38/00* (2006.01)
*A61P 31/04* (2006.01)
*A23B 7/148* (2006.01)
*A23B 7/154* (2006.01)
*A23L 3/36* (2006.01)

(52) U.S. Cl. ......... 514/2.4; 426/106; 426/323; 426/335; 530/360

(58) Field of Classification Search .................. None
See application file for complete search history.

(56) References Cited

U.S. PATENT DOCUMENTS
4,992,420 A * 2/1991 Neeser ............................ 424/48
2004/0214754 A1* 10/2004 Ellis et al. ......................... 514/8

FOREIGN PATENT DOCUMENTS
WO    WO 94/15952      *  7/1994
WO    WO 2005/037248   *  4/2005

* cited by examiner

*Primary Examiner* — Marcela M Cordero Garcia
(74) *Attorney, Agent, or Firm* — The PL Law Group, PLLC

(57) ABSTRACT

An inhibitor against the formation of biofilm includes κ-casein macropeptide. The inhibitor prevents or reduces the formation of a biofilm by inhibiting attachment or attachment/invasion followed by biofilm formation on the abiotic or biotic surfaces by *L. monocytogenes*. The inhibitor can be applied as a food or pharmaceutical additive, a detergent for food or equipments for manufacturing food or pharmaceutics as well as a packing material for food or pharmaceutics.

7 Claims, 9 Drawing Sheets

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: SEQUENCE OF PCR PRIMERS

<400> SEQUENCE: 1
caaactgcta acacagctac t                                              21

<210> SEQ ID NO 2
<211> LENGTH: 21
<212> TYPE: DNA
<213> ORGANISM: Artificial Sequence
<220> FEATURE:
<223> OTHER INFORMATION: SEQUENCE OF PCR PRIMERS

<400> SEQUENCE: 2
gcacttgaat tgctcttatt g                                              21

<210> SEQ ID NO 3
<211> LENGTH: 20
<212> TYPE: DNA
<213> ORGANISM: Artificial Sequence
<220> FEATURE:
<223> OTHER INFORMATION: SEQUENCE OF PCR PRIMERS

<400> SEQUENCE: 3
cggaggttcc gcaaaagatg                                                20

<210> SEQ ID NO 4
<211> LENGTH: 20
<212> TYPE: DNA
<213> ORGANISM: Artificial Sequence
<220> FEATURE:
<223> OTHER INFORMATION: SEQUENCE OF PCR PRIMERS

<400> SEQUENCE: 4
cctccagagt catcgatgtt                                                20

<210> SEQ ID NO 5
<211> LENGTH: 20
<212> TYPE: DNA
<213> ORGANISM: Artificial Sequence
<220> FEATURE:
<223> OTHER INFORMATION: SEQUENCE OF PCR PRIMERS

<400> SEQUENCE: 5
gggaaatttg acactgcgtt                                                20

<210> SEQ ID NO 6
<211> LENGTH: 20
<212> TYPE: DNA
<213> ORGANISM: Artificial Sequence
<220> FEATURE:
<223> OTHER INFORMATION: SEQUENCE OF PCR PRIMERS

<400> SEQUENCE: 6
attttcgggt agtccgcttt                                                20

<210> SEQ ID NO 7
<211> LENGTH: 20
<212> TYPE: DNA

```
<213> ORGANISM: Artificial Sequence
<220> FEATURE:
<223> OTHER INFORMATION: SEQUENCE OF PCR PRIMERS

<400> SEQUENCE: 7
cctagcaggt ctaaccgcac                                               20

<210> SEQ ID NO 8
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 8
tctctaattt ggttatgccc                                               20

<210> SEQ ID NO 9
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 9
aaagcacgat ttcatgggag                                               20

<210> SEQ ID NO 10
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 10
acatagcctt gtttggtcgg                                               20

<210> SEQ ID NO 11
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 11
gacgaaaatc ccgaagtgaa                                               20

<210> SEQ ID NO 12
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 12
ctagcgaagg tgctgtttcc                                               20

<210> SEQ ID NO 13
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 13
cgagcaaaac agcaacgata                                               20
```

```
<210> SEQ ID NO 14
<211> LENGTH: 20
<212> TYPE: DNA
<213> ORGANISM: Artificial Sequence
<220> FEATURE:
<223> OTHER INFORMATION: SEQUENCE OF PCR PRIMER

<400> SEQUENCE: 14
ccgcggacat catttaatgt                                           20
```

US 8,383,582 B2

INHIBITOR AGAINST FORMING BIOFILM COMPRISING κ-CASEIN MACROPEPTIDE

BACKGROUND

1. Field of the Invention

The present invention relates to an inhibitor against biofilm formation of *Listeria monocytogenes* on abiotic or biotic surfaces.

2. Description of the Related Art

Microorganisms can attach to various surfaces and produce a biofilm, which is an aggregate of microorganisms in which cells adhere to each other and/or to an abiotic or biotic surface. Numerous studies have reported that biofilms include a complex multicellular structure; the mass of microcolonies in a single layer or with vertical and horizontal channels allows liquid flow and dispersion of nutrients and waste components.

According to the World Health Organization (2000), *Listeria monocytogenes* is one of the major food-related microorganisms causing foodborne diseases. This bacterium can adhere to the inert surfaces found in the food-processing environment. Its bio-film is a potential, chronic source of microbial contamination, which may compromise the food quality and pose a significant health hazard. Therefore, greater understanding of the interaction between microorganisms and food-processing surfaces is required.

The adhesion of *L. monocytogenes* to food-processing surfaces influences the hydrophobic interactions between the surface material and the outer surface components of the bacterium, rather than being a specific ligand-receptor process. Several researchers have suggested that flagella play a major role in the initial adhesion of higher numbers of *L. monocytogenes* cells to glass and stainless steel compared with nonmotile cells. In *L. monocytogenes*, flagella biosynthesis is dependent on temperature and regulated by a distinctly different mechanism from the well-described hierarchical regulation of gram-negative bacteria. Thus, at the mammalian host physiologic temperature of 37° C., most *L. monocytogenes* strains do not produce flagella and are nonmotile, because of MogR-induced repression of flagellar gene transcription at this temperature. In contrast, at 30° C. and below, the bacterium is motile because MogR is inhibited by its antirepressor, GmaR, permitting flagellar gene transcription. Therefore, *L. monocytogenes* strains have variable abilities to produce biofilms depending on their growth conditions.

As one of the methods for inhibiting bio-film formation, pretreatment of surfaces with protein has been shown to result in lower numbers of adhering microorganisms. Over the past decade, several strategies for preventing microorganism adhesion and biofilm formation on surfaces have been proposed. Most of them focus on surface modification to inhibit adhesion by adsorption of antimicrobial proteins or compounds such as nisin, lysozyme, benzalkonium chloride, silver, or chlorhexidine.

Moreover, *L. monocytogenes* causes commonly called listeriosis, serious illness, including meningitis, septicemia and stillbirth, with a mortality rate of up to 30%. Listeriosis generally affects the elderly, neonates, pregnant and immune-compromised people. This microorganism often found in food elsewhere in nature having been isolated from a variety of sources including soil, vegetation, silage, fecal material, sewage, water, and in the intestines of healthy animals, including humans. Four serotypes (4b, ½a, ½b, and ½c) among 13 known serotypes have been isolated from a wide range of foods. Three of these serotypes (4b, ½a, and ½b) are associated with the majority of human listeriosis. Recently, numerous outbreaks of febrile gastroenteritis have also been reported in healthy persons who ingested *L. monocytogenes* contaminated cheese or delicatessen meat. Symptoms of the febrile gastroenteritis are diarrhea, fever, headache, stomach cramps, and vomiting. However, patho/physiological features or the factors that influence the infectious dose and the occurrence and course of infection still need to be clarified.

SUMMARY

According to an aspect of the present invention, an inhibitor against attachment or attachment/invasion followed by biofilm formation by *L. monocytogenes* on abiotic or biotic surfaces, includes κ-casein macropeptide (CMP).

According to an aspect of the present invention, an additive for food or pharmaceuticals includes an inhibitor having κ-casein macropeptide.

According to an aspect of the present invention, a detergent for washing food or equipment for preparing food or pharmaceuticals includes an inhibitor containing κ-casein macropeptide.

According to an aspect of the present invention, a packing material for food or pharmaceutical includes an inhibitor containing κ-casein macropeptide.

According to an aspect of the present invention, a method for inhibiting biofilm formation by *Listeria monocytogenes* includes the step of adding κ-casein macropeptide to an abiotic or biotic surface.

According to an aspect of the present invention, an inhibitor including κ-casein macropeptide efficiently inhibits attachment or attachment/invasion followed by biofilm formation by *L. monocytogenes* on abiotic surfaces such as surfaces of equipments for preparing food or pharmaceuticals, or biotic surfaces such as surfaces of cells of mammalian including humans.

An inhibitor according to the present invention can decrease threats to our health and improve quality of food or pharmaceuticals by preventing sources of poisoning as well as listeriosis.

Also, an inhibitor according to the present invention can be applied as additives for food or pharmaceuticals, detergents for washing food or equipments for preparing food or pharmaceuticals, and packing materials for food or pharmaceuticals.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
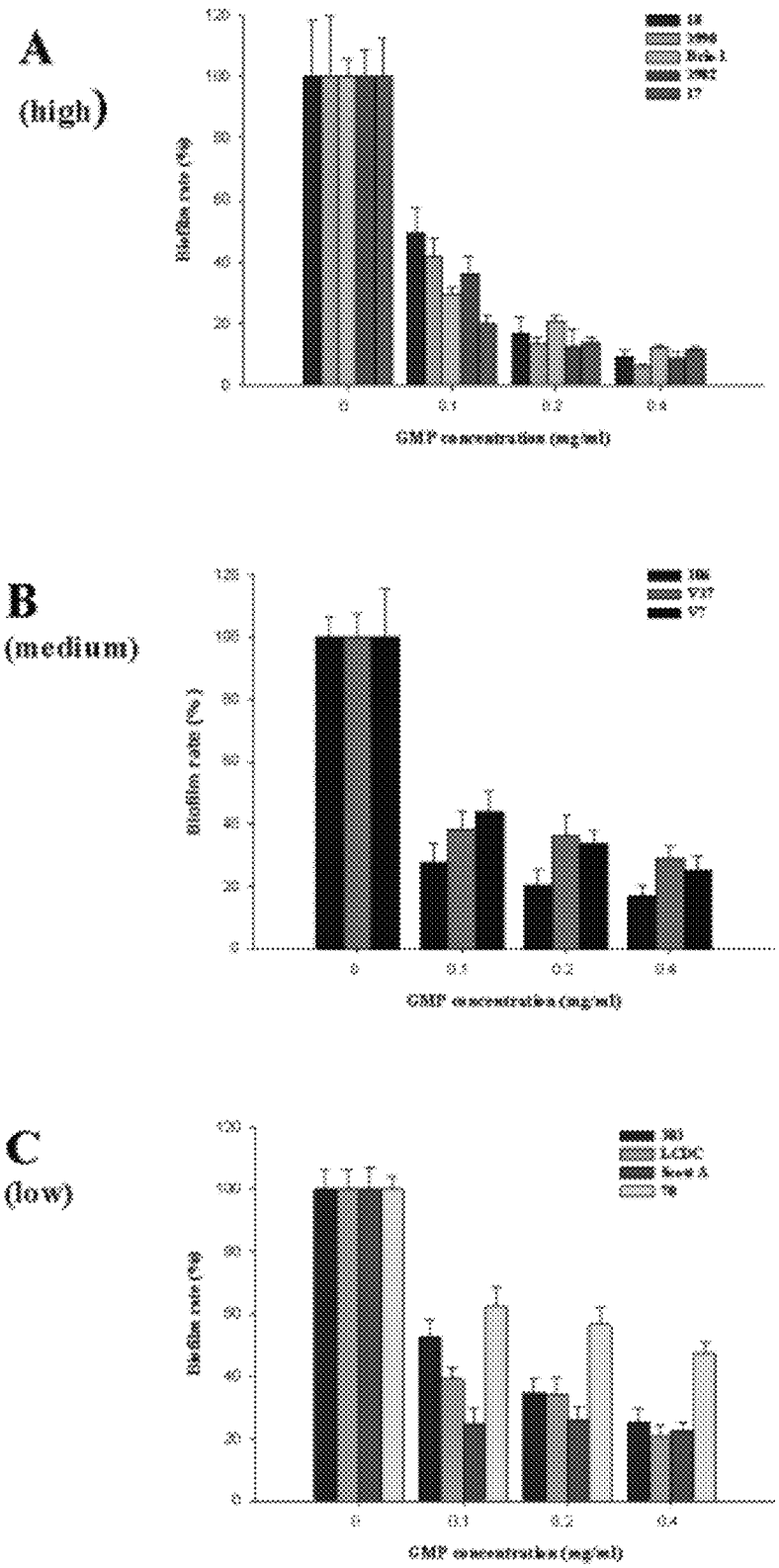
FIG. 1 shows inhibitory effects of active components CMP (0, 0.1, 0.2, and 0.4 mg/ml) on the biofilm formation of *L. monocytogenes* on the 96 well polyvinyl chloride (PVC) as abiotic surfaces under static aerobic growth conditions in MWB for 24 h, wherein (A) shows high inhibition, (B) shows medium inhibition, and (C) shows low inhibition.

According to one embodiment of the present invention, there is provided an inhibitor against forming biofilm by *L. monocytogenes*, and includes κ-casein macropeptide (CMP).

κ-casein macropeptide is a glycomacropeptide separated from κ-casein which is one of the milk proteins named caseinoglycopeptide.

κ-casein macropeptide is the only protein containing saccharide among the milk proteins, in which phosphate and carbohydrate were combined with amino acid residues.

Carbohydrates being combined to κ-casein are N-acetyl neuraminic acid, galactose, N-acetylgalactosamine, etc., which are combined to the threonine or serin residue as a type of o-glycoside in the area of amino acid sequence 127-141 as a type of tri or tetra saccharide.

Also, it is presumed that κ-casein contains at least one phosphate group and about 40% of the total κ-casein do not contain carbohydrate group. Two macro-peptides are formed by decomposing combination between the $105^{th}$ methionine and the $106^{th}$ phenylalanine of κ-casein using chymosin. One of the two, C-terminal part of K-casein is para-κ-casein and the other hydrophilic N-terminal part of κ-casein is κ-casein macropeptide.

κ-casein macropeptide used in the present invention, for example, may be prepared from κ-casein which is separated from acid casein by defatting raw milk by treating with chymosin (Oh et al., 1997; Oh et al., 2005). Also κ-casein macropeptide may be a product being on the market.

By adding the κ-casein macropeptide, biofilm formation caused by attachment on the abiotic surfaces and attachment and invasion on the biotic surfaces by *L. monocytogenes* is inhibited.

According to an embodiment of the present invention, there is provided a food additive and a pharmaceutical additive each including the foregoing inhibitor containing κ-casein macropeptide which is a natural compound.

The food additive or the pharmaceutical additive may further include one or more selected from nutritional supplements, vitamins, minerals (electrolyte), synthetic and natural flavoring agents, coloring agents, enhancing agents (cheese, chocolate, etc.), pectic acid and its salts, alginic acid and its salts, organic acids, protective colloidal thickening agents, pH control agents, stabilizers, preservatives, glycerin and alcohols.

According to an embodiment of the present invention, there is provided a detergent for food or for equipments for manufacturing food or pharmaceutics, wherein the detergent includes the foregoing inhibitor.

According to an embodiment of the present invention, there is also provided a packing material, for example, as an inner coating contacted directly with food or pharmaceutics.

The inhibitor according to an embodiment of the present invention can decrease threats to our health and improve quality of food or pharmaceuticals by preventing sources of poisoning as well as listeriosis.

An embodiment of the present invention will be described by the following examples. However, these examples are provided for illustrative purposes but are not construed to restrict the scope of the present invention as defined by the appended claims.

EXAMPLES

Example 1

*L. monocytogenes* Strain and Growth

*L. monocytogenes* pathogenic bacterial strains used in this invention (TABLE 1) were obtained from Dr. Frank's Laboratory, University of Georgia (Athens, Ga., USA). The stock cultures were maintained at −80° C. in tryptic soy broth (Difco, Sparks, Md., USA) supplemented with 0.6% yeast extract (TSBYE) containing 25% glycerol, used as a cryoprotectant. Before testing, all the strains were subcultured in TSBYE at 37° C. for 18 h. Cultures of *L. monocytogenes* were harvested by centrifugation (8,000×g, 10 min, 4° C.) and the cells were rinsed thrice with phosphate buffered saline (PBS; 1.2688 g disodium phosphate, 0.1 g monosodium phosphate, 0.2113 g monopotassium phosphate, and 7.65 g sodium chloride per liter; pH 7.2).

TABLE 1

| Strains | Serotype | Source | Reference |
|---------|----------|--------|-----------|
| 17 | 4b | Environmental | Folsom et al. (2006) |
| 18 | ND | Environmental | Folsom et al. (2006) |
| 70 | 4b | Environmental | Folsom et al. (2006) |
| 106 | 4b | Environmental | Folsom et al. (2006) |
| 303 | 1/2a | Monkey (clinical) | Folsom et al. (2006) |
| 3982 | 4b | Jalisco cheese outbreak | Folsom et al. (2006) |
| 3990 | 4b | Vaucherin cheese outbreak | Folsom et al. (2006) |
| V7 | 1/2a | Raw milk | Jaradat et al. (2003) |
| V37 | 4b | Bulk milk | Ravishankar et al. (2000) |
| Brie-1 | 1/2b | Brie cheese | Chiu et al. (2006) |
| LCDC | 4b | Cabbage outbreak | Folsom et al. (2006) |
| Scott A | 4b | Human (clinical) | Fleming et al. (1985) |

ND: Not determined

Experimental Example 2

Inhibition of Adhesion and Biofilm Formation by *L. monocytogenes* on Abiotic Surfaces 2-1. Biofilm Formation on Plastic and Glass Surfaces Under Static Condition The quantification of biofilm production on plastic microtiter plates and glass tubes was based on a previously described method (Djordjevic et al., 2002). As abiotic surfaces for biofilm formation, 96-well polyvinyl chloride (PVC) microplates (BD Biosciences, San Jose, Calif., USA) and Pyrex glass tube (10 mm by 20 mm) were used. Overnight cultures of 12 strains of L. monocytogenes were twice washed with PBS and inoculated at $10^6$ CFU/ml in modified Welshimer's broth (MWB) supplemented different concentrations of CMP (Davisco Foods International, Inc., MN, USA; 0.1, 0.2, and 0.4 mg/ml or 1.0, 2.0, and 4.0 mg/ml). After incubation at 30° C. without agitation for 24 and 48 h, the microplates were twice rinsed thoroughly with double-distilled water, and a 0.1% (w/v) solution of crystal violet (CV) was added to stain the attached cells. Following staining at room temperature for 30 min, CV was removed and the wells were rinsed with double-distilled water thrice. After the microplates were air dried, the dye was solubilized with 95% ethanol solution. The absorbance at 595 nm of the solubilized dye was subsequently determined by using an enzyme-linked immunosorbent assay (ELISA) plate reader (Molecular Devices, Sunnyvale, Calif., USA). An equal volume of 95% ethanol was added in the control wells.

Figure 2:
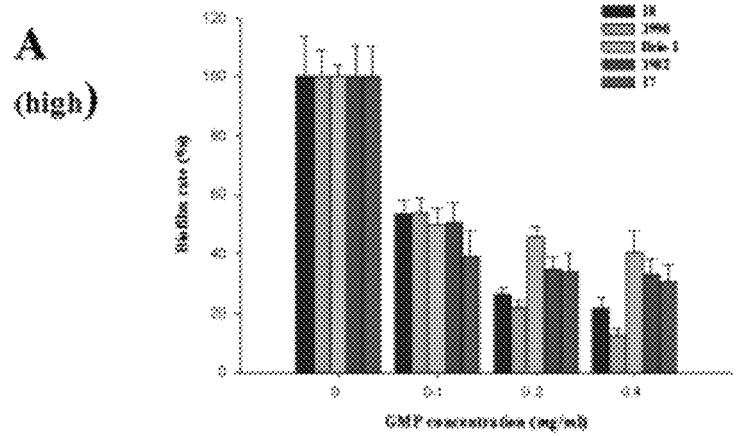
FIG. 2 shows inhibitory effects of active components CMP (0, 0.1, 0.2, and 0.4 mg/ml) on the biofilm formation by *L. monocytogenes* on the 96 well polyvinyl chloride (PVC) as abiotic surfaces under static aerobic growth conditions in MWB for 48 h, wherein (A) shows high inhibition, (B) shows medium inhibition, and (C) shows low inhibition.
Figure 2:
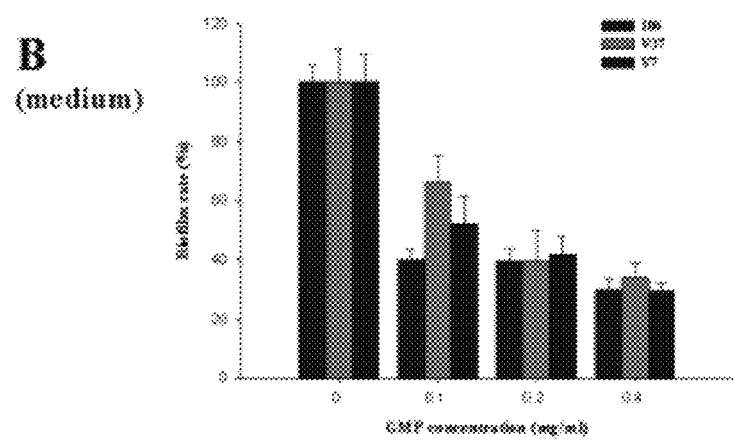
Figure 2:
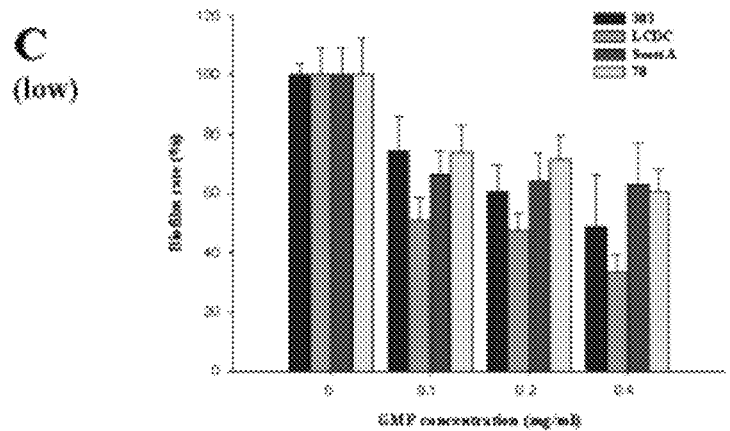

Inhibitory effects of active components CMP on the biofilm formation by L. monocytogenes was illustrated in TABLE 2 and FIGS. 1 and 2.

TABLE 2

A

| Strains | Concentration (mg/ml) | | | |
|---|---|---|---|---|
| | 0 | 1 | 2 | 4 |
| 18 | 100 ± 17.96 | 2.85 ± 0.51 | 2.21 ± 0.31 | 2.24 ± 0.25 |
| 3990 | 100 ± 19.57 | 3.00 ± 0.29 | 3.36 ± 0.52 | 3.79 ± 0.53 |
| Brie-1 | 100 ± 5.57 | 2.34 ± 0.35 | 2.17 ± 0.39 | 2.28 ± 0.34 |
| 3982 | 100 ± 8.79 | 5.18 ± 0.88 | 4.62 ± 0.50 | 5.48 ± 0.75 |
| 17 | 100 ± 12.41 | 9.42 ± 1.49 | 6.55 ± 0.55 | 6.54 ± 0.75 |
| 106 | 100 ± 6.68 | 10.10 ± 2.25 | 10.53 ± 1.96 | 11.64 ± 2.03 |
| V37 | 100 ± 7.46 | 10.23 ± 1.23 | 10.16 ± 0.73 | 11.25 ± 0.61 |
| V7 | 100 ± 15.38 | 13.05 ± 1.56 | 12.16 ± 0.83 | 12.71 ± 1.74 |
| 303 | 100 ± 6.13 | 17.33 ± 2.44 | 13.43 ± 1.81 | 14.54 ± 0.98 |
| LCDC | 100 ± 5.97 | 20.46 ± 4.00 | 15.64 ± 1.70 | 15.01 ± 2.53 |
| Scott A | 100 ± 6.93 | 24.44 ± 4.24 | 17.16 ± 1.87 | 18.65 ± 3.04 |
| 70 | 100 ± 3.86 | 46.31 ± 5.13 | 24.48 ± 3.13 | 22.05 ± 3.74 |

B

| Strains | Concentration (mg/ml) | | | |
|---|---|---|---|---|
| | 0 | 1 | 2 | 4 |
| 18 | 100 ± 13.39 | 24.16 ± 6.51 | 16.80 ± 1.68 | 14.76 ± 2.21 |
| 3990 | 100 ± 8.73 | 16.47 ± 2.25 | 13.83 ± 4.21 | 13.71 ± 1.67 |
| Brie-1 | 100 ± 3.98 | 8.44 ± 1.52 | 8.60 ± 2.12 | 7.93 ± 0.74 |
| 3982 | 100 ± 10.55 | 53.61 ± 13.36 | 28.04 ± 8.08 | 26.52 ± 2.77 |
| 17 | 100 ± 10.16 | 5.86 ± 2.60 | 4.59 ± 2.60 | 7.65 ± 3.26 |
| 106 | 100 ± 5.85 | 17.08 ± 6.41 | 16.60 ± 5.54 | 17.01 ± 6.30 |
| V37 | 100 ± 11.29 | 62.46 ± 13.21 | 48.49 ± 11.61 | 40.72 ± 3.52 |
| V7 | 100 ± 9.47 | 21.33 ± 2.03 | 22.50 ± 3.06 | 24.19 ± 4.94 |
| 303 | 100 ± 4.01 | 32.61 ± 12.03 | 45.13 ± 19.21 | 31.08 ± 8.00 |
| LCDC | 100 ± 8.95 | 30.22 ± 4.93 | 32.04 ± 5.20 | 32.41 ± 7.02 |
| Scott A | 100 ± 9.13 | 71.54 ± 12.99 | 58.13 ± 13.31 | 70.23 ± 18.85 |
| 70 | 100 ± 12.44 | 41.50 ± 11.17 | 33.08 ± 6.13 | 24.36 ± 3.37 |

(A) 24 h,
(B) 48 h
(☐ : high inhibition, ☐ : medium inhibition, ☐ : low inhibition)

For the PVC microplates that contained 1, 2, or 4 mg/ml of CMP, L. monocytogenes biofilms significantly decreased by <90% compared to the control. The twelve strains were classified into three groups of high, medium, and low inhibition by the inhibitory rates of biofilm formation at 24 h incubation as follows: i) 90%≦inhibition rate represent high inhibition; ii) 87%≦inhibition rate<90% represent medium inhibition; iii) inhibition rate<87% represent low inhibition. For the inhibition of L. monocytogenes biofilm formation by CMP, the high inhibition group contained L. monocytogenes 18, 3990, Brie-1, 3982, and 17; the medium inhibition group contained 106, V37, and V7; and the low inhibition group contained 303, LCDC, Scott A, and 70. However, no significant differences were clearly observable among the tested concentrations of CMP. Therefore, when low concentrations of CMP (0.1, 0.2, or 0.4 mg/ml) were used, profound inhibitory effects on biofilm formation were observed at the concentration of 0.4 mg/ml.

Figure 3:
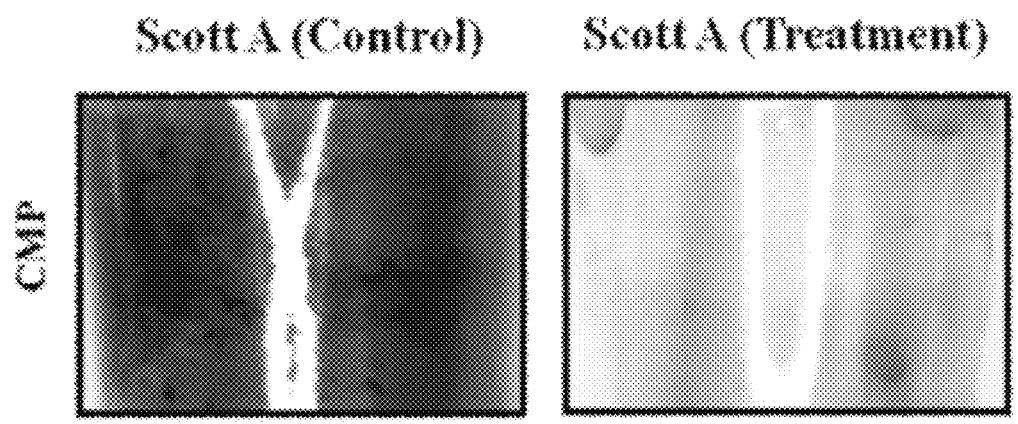
FIG. 3 shows microscopic analysis of inhibitory effects on biofilm formation by *L. monocytogenes* Scott A incubated in PVC microtitre plates in MWB for 24 h in the presence or absence of CMP (0.4 mg/ml)
Figure 4:
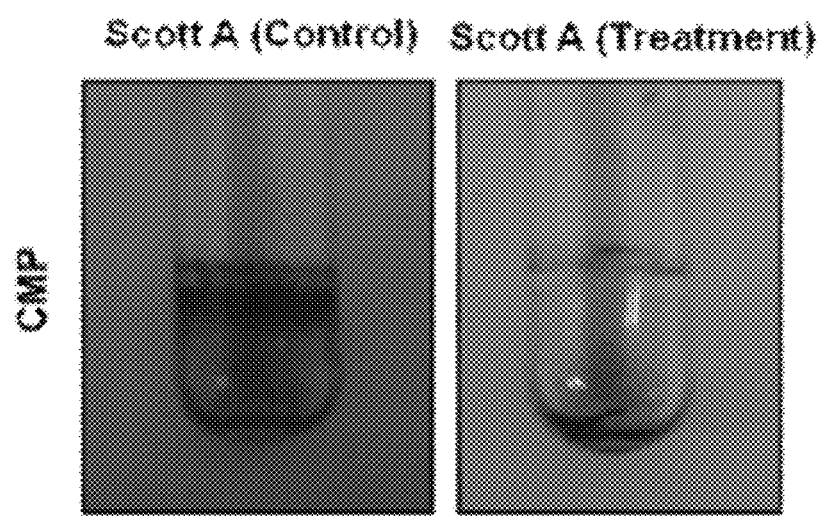
FIG. 4 shows microscopic analysis of inhibitory effects on biofilm formation by *L. monocytogenes* Scott A incubated in glass tubes in MWB for 24 h in the presence or absence of CMP (0.4 mg/ml)

In addition, biofilm formations on PVC microtiter plates and glass tube by L. monocytogenes incubated in MWB for 24 h in the presence or absence of CMP (0.4 mg/ml) were analyzed using light microscopy and microscopic analyses were illustrated in FIGS. 3 and 4, respectively. L. monocytogenes had formed a biofilm which is a clear ring-type aggregates in the well just below the interface of air and liquid, and only a small number of L. monocytogenes Scott A cells had attached after 24 in the presence of CMP (0.4 mg/ml).

Also CMP did not significantly affect the growth yields of L. monocytogenes in MWB at 30° C. (data not shown). Therefore, the biofilm inhibition in this invention did not result from a growth defect due to bactericidal activity of CMP. This result suggested that CMP are potentially useful in preventing the biofilm formation on PVC and glass surfaces under the static condition, especially in the food industry.

2-2. Flow Chamber Biofilm Assays

Under continuous flow conditions, biofilms were grown in glass capillary tubes by using a slight modification of the previously described method (Purevdorj et al., 2002). The flow chambers, with individual channel dimensions of 3 mm×3 mm×50 mm (Stovall Life Sciences, Inc., Greensboro, N.C., USA), were inoculated with 1 ml (~$10^9$ CFU/ml) of the overnight cultures of L. monocytogenes grown in TSBYE. The inoculum was injected to fill the inside of the glass tubes by using a syringe. The tubing upstream of the glass tube was clamped, and the system allowed standing without flow for 30 min at room temperature. After inoculation, the capillary tubes were mounted on a standard microscope slide. The system was switched to continuous culture mode by delivering MWB to the home-made carboy with a flow rate of 0.1 ml/min at 30° C. The CMP was added at both inoculation and in the fresh medium at the most effective concentration to investigate the inhibitory effects on L. monocytogenes biofilm formation. The biofilms developed in the flow chambers were monitored by using transmitted light and 10× objective lenses with an Olympus CH2 microscope (Olympus, Tokyo, Japan).

Figure 5:
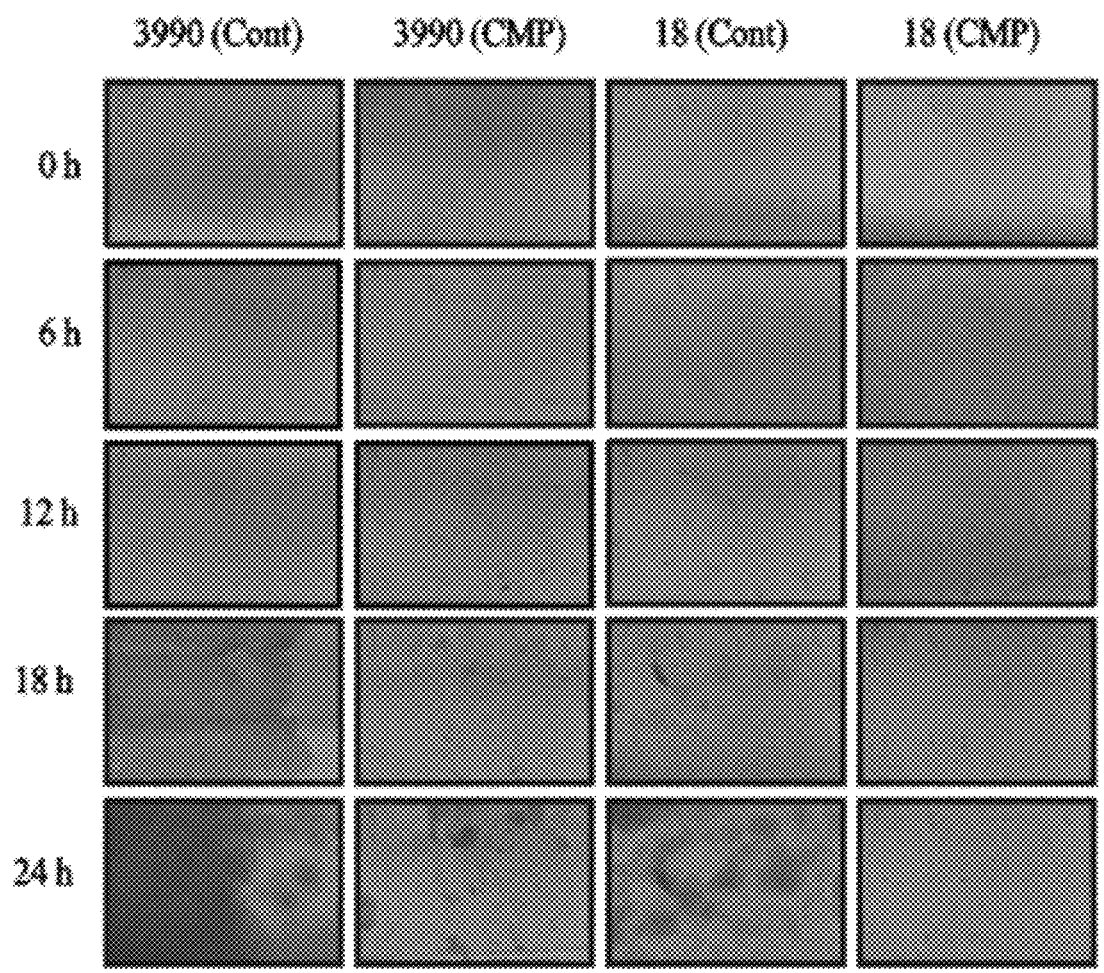
FIG. 5 shows quantification of biofilm formation by *L. monocytogenes* 3990 and 18 using glass capillary tubes and a continuous flow system in the presence of 0.4 mg/ml CMP for 24 h.

Quantification of biofilm formation (such as biofilm development and architecture) by L. monocytogenes 3990 and 18 using glass capillary tubes and a continuous flow system in the presence of 0.4 mg/ml CMP for 24 h was illustrated in FIG. 5. In glass capillary tubes, L. monocytogenes biofilm formation in the presence of CMP was only observed with decreased biomass compared to control. In the absence of CMP, cells attached to the glass surface and began to make cell clusters within 12 h, in a same manner with control. These cell clusters matured to larger organized microcolonies within 18 h and formed a biofilm very thick. Whereas, when 0.4 mg/ml of CMP was added, very few microcolonies or aggregates were seen within same incubation times; in addition, only several small dispersed cell clusters were seen. These results suggest that CMP may have displays anti-biofilm activity by weakening cell-surface modifications (initial attachment), but also by reducing cell-surface interactions (continuous-flow biofilm formation).

2-3. Biofilm Cell and Protein Extraction for Two-Dimensional Gel Electrophoresis This biofilm formation protocol was adapted from that used for the microtiter plate assay in this invention, to obtain a sufficient quantity of biofilm cells for two-dimensional gel electrophoresis (2-DE). Biofilms were prepared by using a slight modification of a previously described method (Ren et al., 2004). L. monocytogenes was grown in TSBYE overnight, and a 2.5 ml overnight culture was washed twice with PBS. Then, the cells were inoculated into a 250-ml shake flask containing 100 ml fresh MWB with or without the effective concentration of CMP on 10 g sterilized glass wool (Pyrex fiber glass; Corning, N.Y., USA). The cells were incubated with shaking (250 rpm in a shaking incubator; Vision Scientific Co., Ltd., Korea) at 30° C. to form a biofilm on the glass wool. After 24 h inoculation, the glass wool was retrieved from the culture, and quickly and gently washed twice in 100 ml of 0.85% sodium chloride buffer (within 30 s) at 4° C. The biofilm cells were removed from the glass wool by sonication in 200 ml of 0.85% sodium chloride buffer at 4° C. for 2 min. The buffer was then centrifuged (8,000×g in a VS-21S MT centrifuge; Vision Scientific Co., Ltd.) for 10 min at 4° C. to precipitate the biofilm cells. These cells were washed twice by centrifugation (8,000×g, 10 min, 4° C.) with 0.85% sodium chloride buffer; the cell pellets were flash-frozen in liquid nitrogen. While sonicating, suspended biofilm cells with an optical density at 600 nm of 2 were harvested by centrifugation (8,000×g) at room temperature for 10 min in an Eppendorf tube. The cell pellets were then flash-frozen in liquid nitrogen and kept at −80° C. until protein extraction.

The biofilm cells harvested from the glass wool were suspended in the same lysis buffer (TE buffer; 40 mM Tris, 1 mM EDTA, pH 8.0) and lysed by using Ultraschallprozessor UP200S (amplification 70, 0.5 cycle; Dr. Hielscher GmbH) 20 times for 30 s on ice. Following sonication, the unlysed cells, cell debris, and glass fibers were removed by centrifugation (8,000×g, 4° C.), and the supernatant fluids were recovered.

Protein samples were precipitated by using the phenol protocol of Hanna et al. (2000). The protein concentration was determined by using the modified Bradford assay method (Ramagli, 1999). The protein samples were stored at −80° C. until proteomic analysis.

2-4. Two-Dimensional Gel Electrophoresis

The method described by Kim et al. (2006) with slight modifications was used for 2-DE. In the first dimension of isoelectric focusing (IEF), precast immobilized pH gradient (IPG) strips, with a nonlinear gradient from pH 3 to 10 (Bio-Rad Laboratories, Richmond, Calif., USA), were rehydrated for 12-18 h with 500 µg of protein in 300 µl of rehydration buffer (8 M urea, 2% CHAPS, 50 mM DTT, 10% isopropanol, 5% glycerol, 0.002% bromophenol blue, 0.2% ampholytes, water). In accordance with the manufacturer's instructions, focusing was performed by using a Protean IEF cell system (Bio-Rad Laboratories) at 20° C. under 60,000 Vh. After IEF, the strips were incubated for 10 min in equilibration buffer I (6 M urea, 2% SDS, 20% glycerol, 130 mM DTT, 0.375 M Tris-HCl [pH 8.8]), followed by another 10 min in equilibration buffer II (6 M urea, 2% SDS, 20% glycerol, 135 mM iodoacetamide, 0.375 M Tris-HCl [pH 8.8]). After equilibration, the strips were transferred to 12.5% sodium dodecyl sulfate (SDS)-polyacrylamide gels (20×22 cm) for running in the second dimension.

The proteins were separated by using a Protean II xi system (Bio-Rad Laboratories) with 20 mA per gel at 4° C. The protein spots were visualized by blue-silver staining (Candiano et al., 2004). The stained gels were then scanned with a densitometric scanner (UTA 2100XL; UMAX, Dallas, Tex., USA), and the spots were analyzed by using the PDQuest software (Bio-Rad Laboratories) in accordance with the manufacturer's instructions. Four gels resulting from two independent experiments were obtained, and two gels of good quality were used for analysis. Only significant spot intensity changes (at least threefold) were considered and selected for mass spectrometric and sequencing analyses.

2-5. In-Gel Protein Digestion

The protein bands of interest were excised and digested in-gel with sequencing grade, modified trypsin (Promega, Madison, Wis., USA) as previously described (Bahk et al., 2004). In brief, each protein spot was excised from the gel, placed in a polypropylene (Eppendorf) tube, and washed 4-5 times (until the gel was clear) with 150 µl of 1:1 acetonitrile and 25 mM ammonium bicarbonate (pH 7.8). The gel slices were dried in a Speedvac concentrator and then rehydrated in 30 µl of 25 mM ammonium bicarbonate (pH 7.8) containing 20 ng of trypsin. After incubation at 37° C. for 20 h, the liquid was transferred to a new tube. Tryptic peptides remaining in the gel matrix were extracted for 40 min at 30° C. with 20 µl of 50% (v/v) aqueous acetonitrile containing 0.1% (v/v) formic acid. The combined supernatants were evaporated in a Speedvac concentrator and dissolved in 8 µl of 5% (v/v) aqueous acetonitrile solution containing 0.1% (v/v) formic acid for mass spectrometric analysis.

2-6. Protein Identification by Mass Spectrometry

The resultant tryptic peptides were separated and analyzed by using reversed-phase capillary high performance liquid chromatography (HPLC) directly coupled to Finnigan LCQ ion trap mass spectrometry (LC-MS/MS) (Zuo et al., 2001, with a slight modification). Both the 0.1×20 mm trapping and the 0.075×130 mm resolving column were packed with Vydac 218MS low trifluoroactic acid C18 beads (5 µl in size, 300 Å in pore size; Vydac, Hesperia, Calif., USA) and placed in-line. After the peptides were bound to the trapping column for 10 min with 5% (v/v) aqueous acetonitrile containing 0.1% (v/v) formic acid, they were eluted with a 50-min gradient of 5-80% (v/v) acetonitrile containing 0.1% (v/v) formic acid at a flow rate of 0.2 µl/min. For MS/MS, a full-mass scan range mode was used (m/z=450-2000). After determining the charge states of an ion on zoom scans, product ion spectra were acquired in MS/MS mode with relative collision energy of 55%.

The individual spectra from MS/MS were processed by using the TurboSEQUEST software (ThermoQuest, San Jose, Calif.). The generated peak list files were used to query either the MSDB or the National Center for Biotechnology Information (NCBI) database by using the MASCOT program (available at http://www.matrixscience.com). Modifications of methionine and cysteine, peptide mass tolerance at 2 Da, MS/MS ion mass tolerance at 0.8 Da, allowance of missed cleavage at 2, and charge states (+1, +2, and +3) were considered. Only significant hits as defined by MASCOT probability analysis were considered initially.

2-7. Statistical Analyses

All experiments were conducted at least in triplicate. The effects of each treatment were analyzed by analysis of variance (ANOVA) followed by Duncan's test with the SAS software package (version 9.1; SAS, Inc., Cary, N.C., USA). The level of significance was defined at $p<0.05$.

Figure 6:
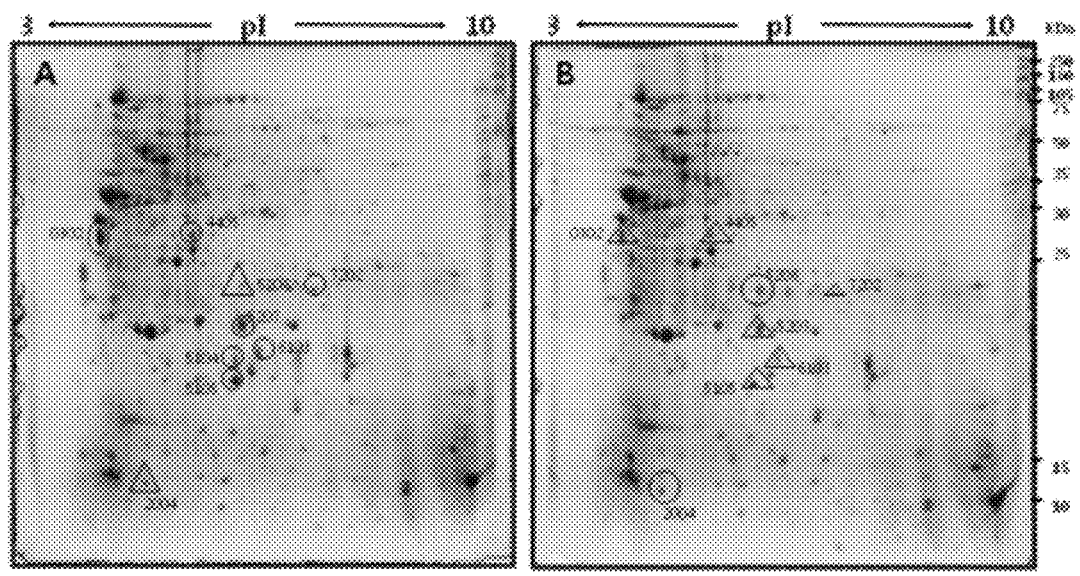
FIG. 6 shows two dimensional gel electrophoresis images of protein extracts of *L. monocytogenes* Scott A biofilm cells, wherein (A) is in the absence of CMP, and (B) is in the presence of 0.4 mg/ml CMP.

Two dimensional gel electrophoresis images of protein extracts of L. monocytogenes Scott A biofilm cells grown in the absence and in the presence of 0.4 mg/ml CMP were illustrated in FIG. 6. A total of approximately about 320 protein spots could be visualized by CBB G-250 staining. Interestingly, total nine protein spots with increase or decrease in amounts were detected from *L. monocytogenes* Scott A in the presence of CMP compared to the control (two and seven spots were up- and down-regulated, respectively). The identified proteins by LC-MS/MS were summarized in TABLE 3.

Then, the cells with adherent bacteria were harvested with trypsin, centrifuged at 10,000×g for 5 min, and suspended in PBS. Adherent *L. monocytogenes* Scott A cells were enumerated on TSBYE and incubated for 48 h at 37° C.

3-3. Invasion Analysis

The invasion of epithelial cells by *L. monocytogenes* Scott A was studied using the gentamicin-based assay described by Bunduki et al. (1993) and Gaillard et al. (1987) with modifications. Briefly, the HT-29 and the AGS cells monolayers ($10^6$

TABLE 3

| No. | Protein | M.W. (Da) | pI | MS[a] | Seq Cov (%) | Accession No. | FC[b] |
|---|---|---|---|---|---|---|---|
| 0302 | enolase [*Listeria monocytogenes* FSL J1-208] | 28242 | 4.64 | 79 | 5 | gi\|255024356 | −3.8 |
| 2004 | glutamine synthetase [*Listeria monocytogenes* LO28] | 19209 | 4.57 | 286 | 36 | gi\|255030735 | +2.4 |
| 4405 | 6-phosphofructokinase [*Listeria innocua* Clip11262] | 34368 | 5.57 | 89 | 5 | gi\|16800674 | −2.8 |
| 5104 | hypothetical protein Smal_0271 [*Stenotrophomonas maltophilia* R551-3] | 21074 | 5.80 | 492 | 53 | gi\|194364049 | V |
| 5105 | conserved hypothetical protein [*Stenotrophomonas maltophilia* K279a] | 21020 | 6.06 | 345 | 27 | gi\|190572457 | −2.0 |
| 5206 | Gap [*Listeria innocua*] | 22054 | 5.55 | 467 | 61 | gi\|224992966 | +2.9 |
| 5207 | hypothetical protein Smal_0271 [*Stenotrophomonas maltophilia* R551-3] | 21071 | 5.80 | 340 | 34 | gi\|194364049 | −2.4 |
| 6103 | glutamine synthetase [*Listeria monocytogenes* LO28] | 19209 | 4.57 | 196 | 24 | gi\|255030735 | −2.0 |
| 7202 | phosphoglycerate mutase 1 family [*Stenotrophomonas maltophilia* R551-3] | 28036 | 6.51 | 499 | 55 | gi\|194364976 | −3.2 |

[a] MS. Mowse score;
[b] FC, Fold difference in biofilm;
[c] U.I: Unidentified.

Example 3

Inhibition of Adhesion and Invasion by *L. monocytogenes* on Mammalian Cells 3-1. Mammalian Cell Culture The human intestinal epithelial cell line HT-29 and the human gastric epithelial cell line AGS were purchased from the Korea Cell Line Bank (KCLB; Seoul, Korea). HT-29 cells have been extensively used as a model system for studying interaction of enteric pathogens with intestinal epithelial cells. All media and fetal bovine serum (FBS) were obtained from Gibco BRL (Life Technologies Inc., Grand Island, N.Y., USA) and JBI (Jeil Biotech services Inc., Seoul, Korea). The HT-29 and AGS cells were grown in RPMI-1640 medium which was supplemented with 10% heat-inactivated FBS. The cells were routinely cultured at 37° C. in 5% $CO_2$ incubator with 6-well or 12-well tissue culture plates for adhesion and invasion assays and in 100-mm-diameter tissue culture plates for RNA isolation.

3-2. Adhesion Analysis

Prior to the adhesion assay, the HT-29 and the AGS cells monolayers were washed three times in pre-warm PBS (25° C.) to remove any culture medium and non-attached cells. The adhesion assays were performed using *L. monocytogenes* Scott A according to the method of Hagman et al. (1999) with modifications. Bacteria were grown overnight at 37° C. in TSBYE. 100 µl of bacteria ($10^8$ and $10^6$ CFU/ml) was added to the HT-29 and the AGS cells monolayers ($10^6$ cells) in 24-well tissue culture plates to obtain a multiplicity of infection (MOI) of 1:1 and 100:1, respectively and the bacteria were incubated for 30 min at 37° C. in the absence or presence of 0.4 mg/ml CMP, respectively. The plates were washed 5 times with pre-warm PBS to remove non-attached bacteria.

cells) were inoculated with 100 µl of the *L. monocytogenes* Scott A suspension ($10^8$ and $10^6$ CFU/ml) and incubated for 1.5 h at 37° C. in the absence or presence of 0.4 mg/ml CMP, respectively. The monolayers were washed with PBS, followed by the addition of 250 µl of 1 mg/ml gentamicin (Sigma) and incubation for an additional 1.5 h. The monolayers were then washed with PBS and lysed with 250 µl of ice-cold 0.1% (v/v) Triton X-100 (Sigma). Appropriate dilutions were plated on TSBYE and incubated for 48 h at 37° C.

Figure 7:
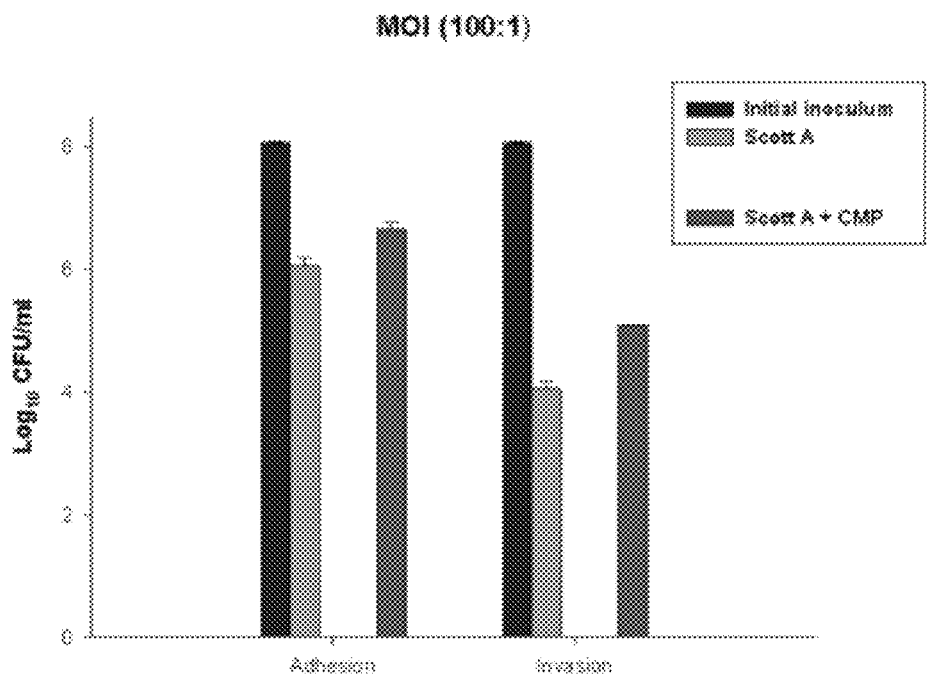
FIG. 7 shows inhibitory effects of active components CMP (0.4 mg/ml) on adhesion and invasion of *L. monocytogenens* Scott A to HT-29 cell.
Figure 7:
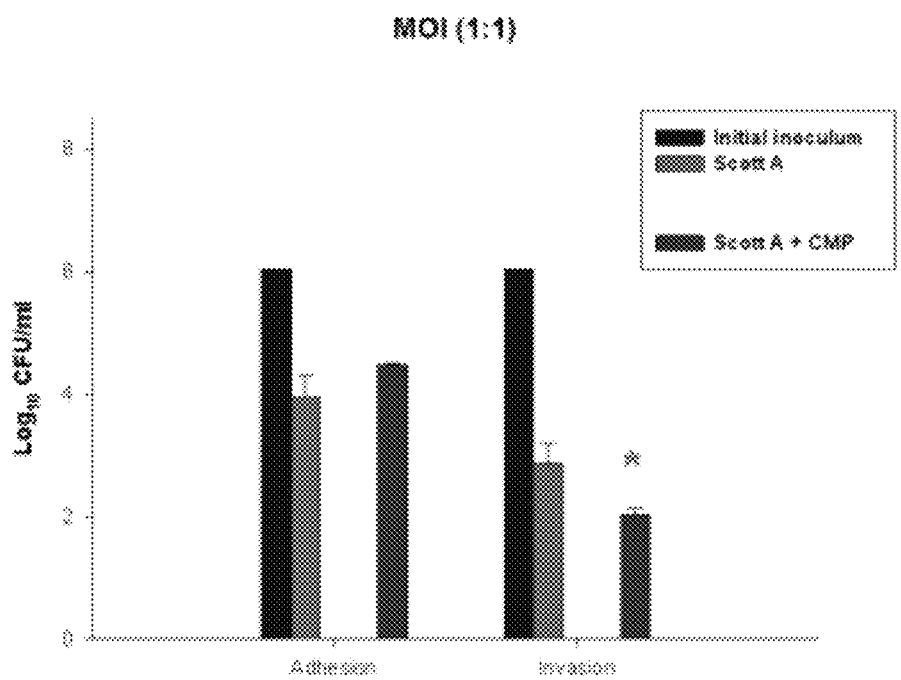
Figure 8:
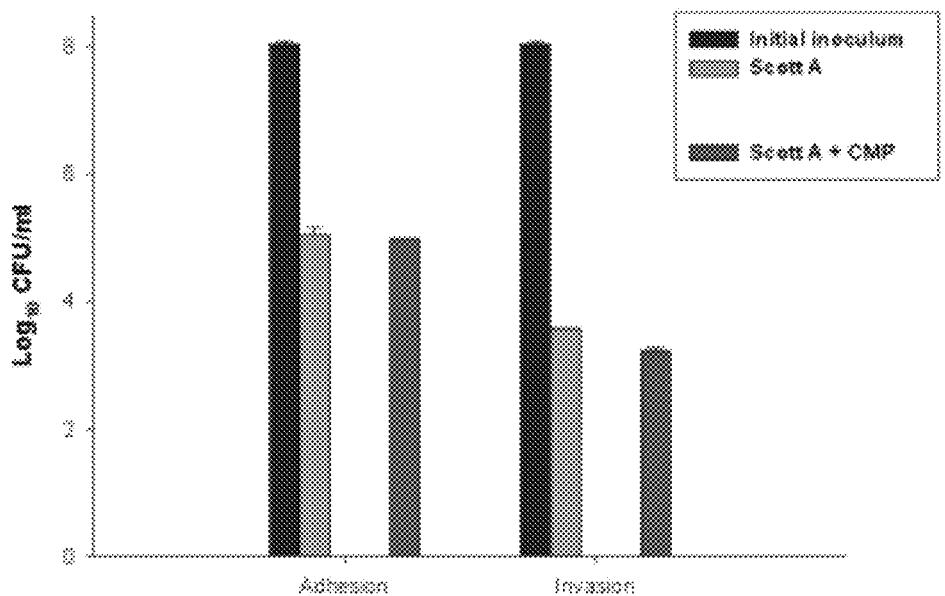
FIG. 8 shows inhibitory effects of active components CMP (0.4 mg/ml) on adhesion and invasion of *L. monocytogenens* Scott A to AGS cell.
Figure 8:
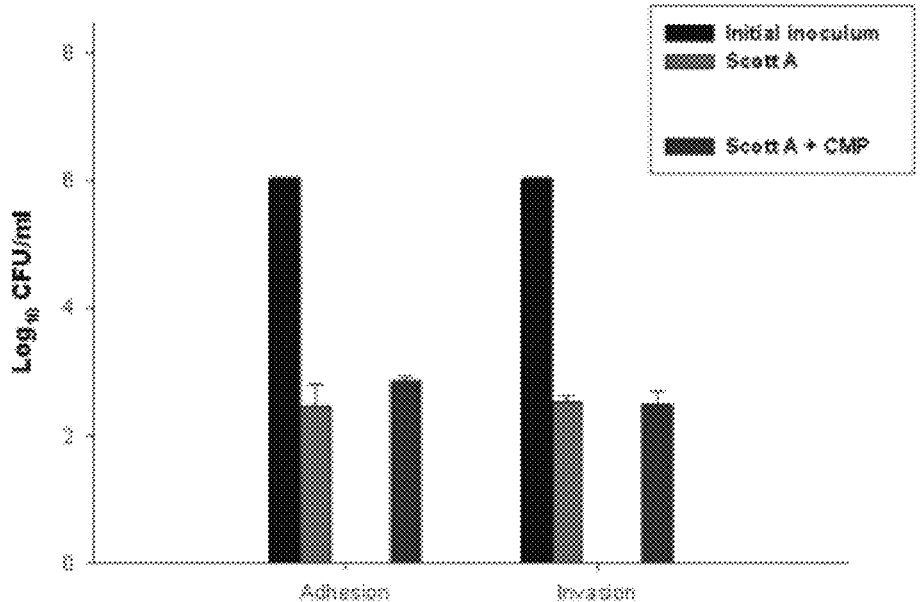

Inhibitory effects of active components CMP (0.4 mg/ml) on adhesion and invasion of *L. monocytogenens* Scott A to HT-29 and AGS cell were illustrated in FIGS. 7 and 8, respectively. As a result, CMP (0.4 mg/ml) was examined with regard to their ability to inhibit the attachment and invasion of *L. monocytogenes* Scott A to HT-29 and AGS cells. In addition, these results suggest that CMP prevented from adhesion and invasion of *L. monocytogenes* Scott A on both HT-29 and AGS cells at the lower MOI.

3-4. Semi-Quantitative RT-PCR Analysis

The regulation of virulence-associated genes was investigated by using semi-quantitative RT-PCR techniques. Total RNA was isolated from the each treated samples using a RNeasy™ Total RNA Kit (Qiagen) with manufacturer's manuals. One µg total RNA was reverse transcribed in 20 µl reaction mixtures with SuperScript™ III First-Strand cDNA Synthesis Kit (Invitrogen, Carlsbad, Calif.). Then, cDNA were then amplified by using Taq DNA polymerase (TaKaRa, Japan). For the iap, denaturation for 5 min at 94° C. was followed by 40 cycles composed of 30 s denaturation at 94° C., 45 s annealing at 60° C. (TABLE 4), and 1 min elongation at 72° C. Except for the iap, denaturation for 5 min at 94° C. was followed by 35 cycles composed of 1 min denaturation at 94° C., 2 min annealing at 60° C. (TABLE 4), and 1 min elongation at 72° C. The last cycle was followed by 10 min final elongation at 72° C. Oligonucleotide (Bioneer, Daejun, Korea) sequences used for the amplification of each gene fragments including expression of proteins (HT-29) are shown in TABLE 4 (Haller et al., 2000). The RT-PCR products were electrophoresed in a 1.5% agarose gel and visualized by ethidium bromide (EtBr) staining. The intensity of each band was determined by densitometric analysis of gels using Kodak DC290 zoom digital camera and Kodak 1D image analysis software (Eastman Kodak Company, Rochester, N.Y., USA).

mined at various time points for 15 days with a light microscopy (Olympus CH30, Tokyo, Japan). Nematodes were considered dead when they failed to respond to tapping of the plate. Each experimental condition was tested in duplicate or triplicate. In analogous experiments, E. coli OP50 was used as controls.

Effects of active components CMP (0.4 mg/ml) on the survivals of Caenorhabditis elegans nematodes living on a lawn of L. monocytogenes Scott A for 15 days were illustrated

TABLE 4

| Genes | Sequence of PCR Primers | Annealing Temp (° C.) | Amplified fragment (bp) |
|---|---|---|---|
| Iap | Forward: 5'-CAA ACT GCT AAC ACA GCT ACT-3' (SEQ ID NO: 1) Reverse: 5'-GCA CTT GAA TTG CTC TTA TTG-3' (SEQ ID NO: 2) | 60 | 371 |
| hlyA | Forward: 5'-CGG AGG TTC CGC AAA AGA TG-3' (SEQ ID NO: 3) Reverse: 5'-CCT CCA GAG TCA TCG ATG TT-3' (SEQ ID NO: 4) | 60 | 234 |
| plcB | Forward: 5'-GGG AAA TTT GAC ACT GCG TT-3' (SEQ ID NO: 5) Reverse: 5'-ATT TTC GGG TAG TCC GCT TT-3' (SEQ ID NO: 6) | 60 | 261 |
| inlA | Forward: 5'-CCT AGC AGG TCT AAC CGC AC-3' (SEQ ID NO: 7) Reverse: 5'-TCT CTA ATT TGG TTA TGC CC-3' (SEQ ID NO: 8) | 60 | 255 |
| inlB | Forward: 5'-AAA GCA CGA TTT CAT GGG AG-3' (SEQ ID NO: 9) Reverse: 5'-ACA TAG CCT TGT TTG GTC GG-3' (SEQ ID NO: 10) | 60 | 146 |
| actA | Forward: 5'-GAC GAA AAT CCC GAA GTG AA-3' (SEQ ID NO: 11) Reverse: 5'-CTA GCG AAG GTG CTG TTT CC-3' (SEQ ID NO: 12) | 60 | 268 |
| plcA | Forward: 5'-CGA GCA AAA CAG CAA CGA TA-3' (SEQ ID NO: 13) Reverse: 5'-CCG CGG ACA TCA TTT AAT GT-3' (SEQ ID NO: 14) | 60 | 129 |

Figure 9:
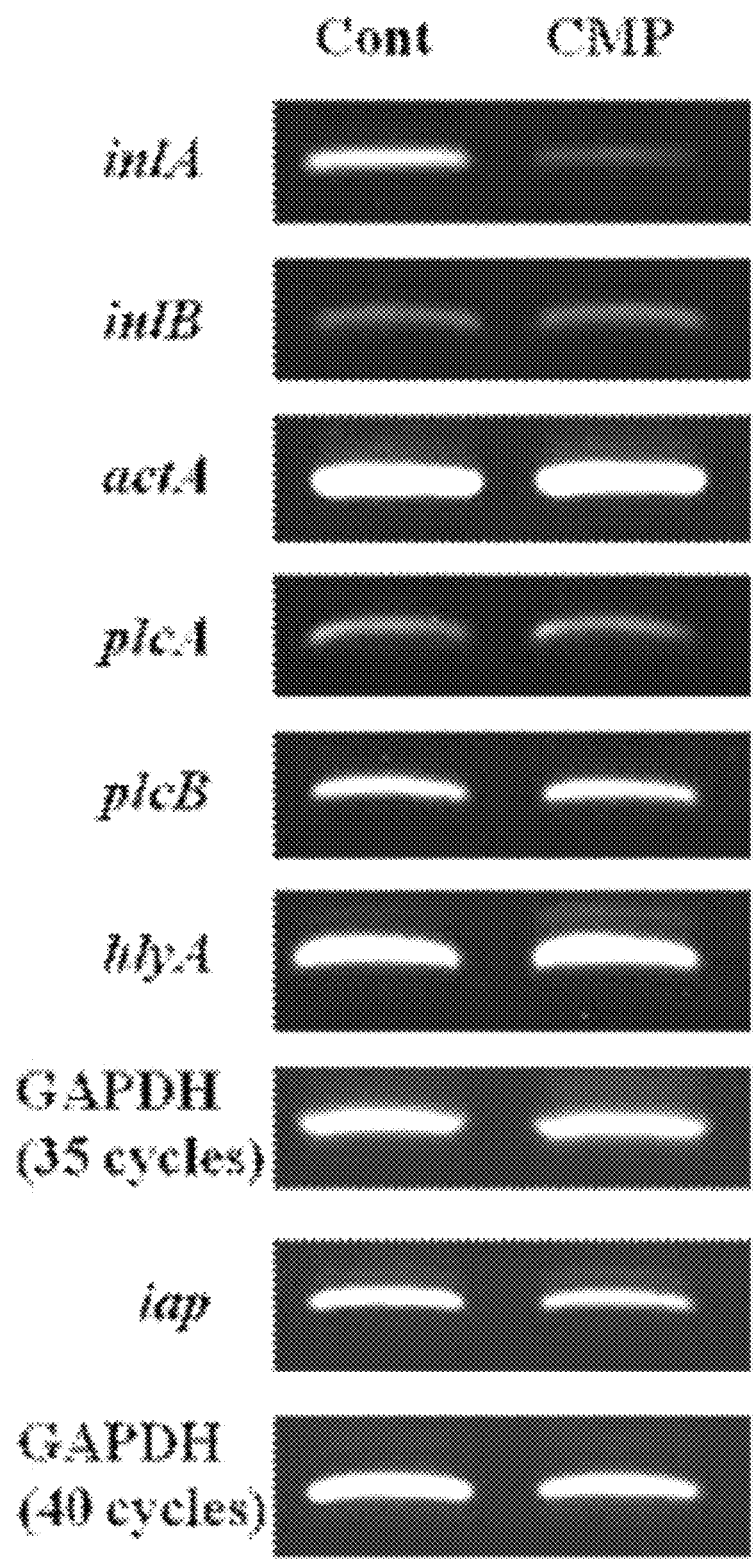
FIG. 9 shows semi-quantitative RT-PCR images of inhibitory effects of active components CMP (0.4 mg/ml) on the virulence-associated genes expression (iap, inlA, inlB, actA, plcA, plcB, and hlyA)

The mRNA levels of virulence-associated genes of L. monocytogenes, such as iap, inlA, inlB, actA, plcA, plcB, and hlyA were observed in the presence of 0.4 mg/ml CMP, and their semi-quantitative RT-PCR images were illustrated in FIG. 9. As a result, inlA, plcB, hlyA, and iap were significantly repressed by the presence of 0.4 mg/ml CMP on the L. monocytogenes Scott A infected HT-29 cells.

3-5. Nematode Caenorhabditis elegans Killing Assay

Figure 10:
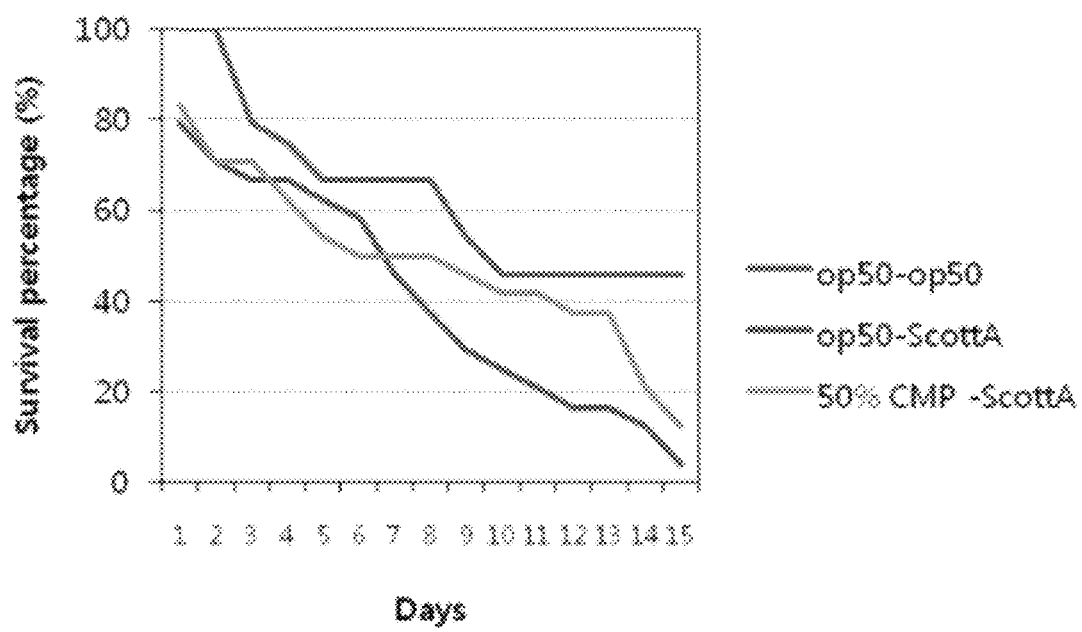
FIG. 10 shows effects of active components CMP (0.4 mg/ml) on the survivals of *Caenorhabditis elegans* nematodes living on a lawn of *L. monocytogenes* Scott A for 15 days.

Caenorhabditis elegans killing assay were performed as initially described by Tenor et al. (2004) with modification. Briefly, L. monocytogenes Scott A was grown in 10 ml of TSBYE culture for overnight. Culture samples (each, 10 μl) were then spread on NGM agar plates (Brenner, 1974; diameter of each, 30 mm). In the present invention, instead of wild-type Bristol N2 worms, we tested killing of C. elegans glp-4 mutant worms. C. elegans glp-4 animals have normal morphology and brood sizes at 15° C. but do not make gonads and are unable to produce eggs at 25° C. (Mylonakis et al., 2002). For each strain, healthy 12 nematodes in L4 stage were transferred from NGM plates seeded with Escherichia coli OP50 to the plates seeded with L. monocytogenes Scott A in the absence or presence of 0.4 mg/ml of CMP and incubated at 25° C. The number of living worms per plate was deterin FIG. 10. It was observed that the group which treated with L. monocytogenes Scott A reduced survival percentage, significantly. There were significant differences between control and treatment group on the survival rates of C. elegans from the first day. Compared to E. coli OP50 as negative control, when C. elegans was placed on a lawn of L. monocytogenes Scott A, only 37.5% of the nematodes were survived for 8 days. On the other hand, 54 and 50% of the worms were survived on the agar medium supplemented with CMP (0.4 mg/ml) for same incubation, respectively.

These results provide some evidence, at least in a part, CMP partially repressed expression of virulence-associated genes from L. monocytogenes Scott A in vivo. In addition, C. elegans was used as host model for L. monocytogenes infection, and CMP was treated to reduce the infection that lead to prolong the viability of the worms. As a result, when CMP treated prolong the survival ability from the infection of L. monocytogenes.

While the present invention has been described with respect to the specific embodiments, it will be apparent to those skilled in the art that various changes and modifications may be made without departing from the spirit and scope of the invention as defined in the following claims.

What is claimed is:

1. A packing material for food or pharmaceuticals, the packing material having an inner surface to be contacted with the food or the pharmaceutical, the inner surface coated with an inhibitor against forming biofilm by *Listeria monocytogenes*, the inhibitor comprising κ-casein macropeptide.

2. A method for inhibiting the formation of a biofilm by *Listeria monocytogenes*, the method comprising: adding κ-casein macropeptide to a surface infected by *Listeria monocytogenes*.

3. The method of claim 2, wherein the surface is an abiotic surface.

4. The method of claim 2, wherein the surface is a biotic surface.

5. The method of claim 2, wherein the surface is the inner surface of a packing material for food or pharmaceuticals.

6. The method of claim 5, wherein the packing material is contacted with food or pharmaceuticals.

7. The method of claim 2, wherein the surface is the inner surface of a piece of equipment for food or pharmaceuticals.

* * * * *